US00PP23997P3

(12) United States Plant Patent
Smith

(10) Patent No.: US PP23,997 P3
(45) Date of Patent: Oct. 15, 2013

(54) ***SALVIA* PLANT NAMED 'GOLDEN GIRL'**

(50) Latin Name: *Salvia hybrida*
Varietal Denomination: Golden Girl

(75) Inventor: M. Nevin Smith, Watsonville, CA (US)

(73) Assignee: CP Delaware, Inc., Wilmington, DE (US)

( * ) Notice: Subject to any disclaimer, the term of this patent is extended or adjusted under 35 U.S.C. 154(b) by 468 days.

(21) Appl. No.: 12/923,371

(22) Filed: Sep. 17, 2010

(65) Prior Publication Data

US 2012/0073025 P1 Mar. 22, 2012

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Susan McCormick Ewoldt
(74) *Attorney, Agent, or Firm* — Buchanan Ingersoll & Rooney P.C.

(57) ABSTRACT

A new and distinct *Salvia* plant of unknown parentage is provided that was discovered in a nursery setting while growing among other *Salvia* plants. Over a long blooming season attractive blossoms are formed that are pale yellow in coloration. The growth habit is compact and bushy. The foliage is large and medium green in coloration. Following pruning, the plant displays a tendency to vigorously regrow. The plant is well suited for providing attractive ornamentation.

1 Drawing Sheet

Botanical/commercial classification: *Salvia hybrida/ Salvia* Plant.

Varietal denomination: cv. Golden Girl.

SUMMARY OF THE INVENTION

The new *Salvia* cultivar of the present invention was discovered during August or September, 2005, while growing in a plant nursery setting among other *Salvia* plants at Watsonville, Calif., U.S.A. The new cultivar is of unknown parentage and likely includes *Salvia jamensis* and *Salvia microphylla* in its ancestry. The new plant was distinguished from other *Salvia* plants growing in the nursery where it was discovered primarily through a study of its distinctive blossom coloration combined with other attractive botanical characteristics identified hereafter. Had the single plant of the present invention not been discovered and carefully preserved, it would have been lost to mankind.

The plant is a perennial that can be grown to advantage without protection in U.S.D.A. Hardiness Zone Nos. 7 to 11.

It was found that the new *Salvia* cultivar possesses the following combination of characteristics:

(a) displays a compact and bushy growth habit,
(b) forms in abundance over a long blooming season attractive blossoms that are pale yellow in coloration,
(c) displays vigorous large medium green foliage,
(d) displays a tendency to vigorously regrow following pruning, and
(e) is well suited for providing attractive ornamentation.

The new cultivar of the present invention can be readily distinguished from other *Salvia* plants, such as the *Salvia madrensis* (non-patented in the United States). *Salvia madrensis* also is yellow flowering but displays a considerably taller growth height (e.g., a height of 1.6 to 2.3 m) unlike the new cultivar of the present invention.

The new cultivar well meets the needs of the horticultural industry and can be grown to advantage as attractive ornamentation in parks, gardens, public areas, and residential landscapes. The pale yellow blossoms contrast nicely with the green foliage.

The new cultivar has been asexually reproduced by the rooting of cuttings for several generations. Root strike from a cutting commonly is observed in approximately 9 days on average. Such asexual reproduction as performed at Watsonville, Calif., U.S.A., and near West Grove, Pa., U.S.A., has demonstrated that the characteristics of the new cultivar are firmly fixed and stable and are strictly transmissible from one generation to another. Accordingly, the new cultivar asexually reproduces in a true-to-type manner from one generation to another.

The new cultivar has been named 'Golden Girl'.

BRIEF DESCRIPTION OF THE PHOTOGRAPH

The accompanying photograph shows as nearly true as it is reasonably possible to make the same, in a color illustration of this character, a close view of a typical specimen of the new cultivar while growing outdoors. The pale yellow blossoms are illustrated as is the attractive large medium green foliage. The pink blossoms in the rear are from another plant and should be disregarded. The plant had been reproduced by the rooting of a cutting and was grown in a greenhouse in a container near West Grove, Pa., U.S.A. The photograph was obtained during July 2010 when the plant was approximately one year of age.

DETAILED BOTANICAL DESCRIPTION

The chart used in the identification of colors is that of The Royal Horticultural Society (R.H.S. Colour Chart) of London, England (1995 Edition or equivalent). Color terminology in common terms sometimes is included as an aid to the reader. Such color terminology is to be accorded its customary dictionary significance. The description is based on the observation of typical specimens of the new cultivar at an age of approximately one year during July 2010 while growing in containers outdoors near West Grove, Pa., U.S.A.

Plant:

*Form.*—Compact and bushy.

*Height.*—Commonly up to approximately 30 cm on average.

*Width.*—Commonly approximately 50 cm on average.

*Growth habit.*—Perennial in U.S.D.A. Hardiness Zone Nos. 7 to 11.

*Branch length.*—Commonly approximately 37 cm on average.

*Branch diameter.*—Commonly approximately 2 mm on average.

*Branch color.*—Near Yellow-Green Group 144B.

*Branch texture.*—Commonly covered with short hairs having lengths of approximately 1 mm resulting in somewhat rough texture.

*Leaf arrangement.*—Opposite.

*Leaf configuration.*—Elliptic to oblong.

*Leaf length.*—Commonly approximately 3 to 3.5 cm on average.

*Leaf width.*—Commonly approximately 2 to 3 cm on average.

*Leaf margin.*—Repand.

*Leaf texture.*—Smooth on both surfaces.

*Leaf blade color.*—Green Group 137C on the upper surface, and Green Group 138B on the under surface.

*Leaf blade apex.*—Acute to obtusely rounded.

*Leaf blade base.*—Mainly obtuse.

*Scent.*—Leaves commonly display a tangy fruity scent when crushed.

*Petiole shape.*—Somewhat flattened.

*Petiole length.*—Variable and commonly approximately 5 to 9 mm.

*Petiole width.*—Commonly approximately 1 to 1.5 mm.

*Petiole color.*—Yellow-Green Group 145A.

Inflorescence:

*Time.*—Prolonged blooming period beginning in May and extending through September.

*Type.*—Terminal raceme.

*Diameter.*—Commonly approximately 1.3 cm on average.

*Length.*—Commonly approximately 2 cm on average.

*Number.*—Commonly up to approximately 50 flowers per plant on average.

*Configuration.*—Tubular, and two-lipped.

*Pedicel length.*—Commonly approximately 3 to 4 mm on average.

*Pedicel width.*—Commonly approximately 2 mm on average.

*Pedicel texture.*—Glabrous, with no observed pubescence.

*Pedicel color.*—Green, Yellow-Green Group 145B.

*Calyx shape.*—Broadly campanulate, and flared towards the apex.

*Calyx rib number.*—Commonly 13, and longitudinally disposed.

*Calyx length.*—Commonly approximately 10 mm on average.

*Calyx width.*—Commonly up to 6 mm.

*Calyx texture.*—Glandular and puberulent on the upper and under surfaces.

*Calyx color.*—On the upper lobe Red-Purple Group 60B at the apex and Yellow-Green Group 145B at the base, and on the lower lobes primarily Yellow-Green Group 145B.

*Calyx lobe number.*—3.

*Calyx upper lobe number.*—1.

*Calyx upper lobe shape.*—Acute.

*Calyx upper lobe length.*—Commonly approximately 4 mm on average.

*Calyx upper lobe width.*—Commonly approximately 4 mm in width.

*Calyx lower lobe number.*—2.

*Calyx lower lobe shape.*—Acute.

*Calyx lower lobe length.*—Commonly approximately 3 mm on average.

*Calyx lower lobe width.*—Commonly approximately 4 mm on average.

*Corolla shape.*—Tubular proximally to two-lipped distally.

*Corolla length.*—Commonly approximately 2.2 to 2.5 cm on average.

*Corolla color.*—The base commonly is near Yellow-White Group 158D, the tube is near Yellow Group 6D, and the lower lip is near Yellow Group 6D.

*Corolla tube length.*—Approximately 23 mm on average.

*Corolla tube width.*—Approximately 3 mm on average.

*Corolla tube depth.*—Approximately 7 mm on average.

*Corolla tube lip number.*—2.

*Corolla upper lip number.*—1.

*Corolla upper lip shape.*—Hood-like.

*Corolla upper lip length.*—Commonly approximately 9 mm average.

*Corolla lower lip length.*—2, suborbicular.

*Corolla lower lip shape.*—Banner-like, and extended downward.

*Corolla lower lip outline.*—Obovate.

*Corolla lower lip length.*—Commonly approximately 12 mm on average.

*Corolla lower lip diameter at tip.*—Approximately 12 mm on average.

*Style length.*—Approximately 2.5 cm on average.

*Style width.*—Commonly approximately 1 mm on average.

*Style attachment site.*—At four-lobed ovary between lobes.

*Stamen number.*—2.

*Stamen shape.*—Seesaw-like.

*Filament length.*—Approximately 6 mm on average.

*Connective length.*—Approximately 12 mm on average.

*Anther length.*—Approximately 2 mm on average.

*Anther width.*—Approximately 1 mm on average.

*Anther color.*—Yellow-Orange Group 16A.

*Anther attachment site.*—At outer end of the connective.

Development:

*Vegetation.*—Vigorous and displays a tendency to quickly regrow following pruning.

*Blooming.*—Displays long blooming season.

*Fertility.*—Not observed with the plants being sterile during observations to date.

*Winter hardiness.*—The plant is a perennial that can be grown in at least U.S.D.A. Hardiness Zone Nos. 7 to 11.

*Disease resistance.*—No particular sensitivity to disease has been encountered during observations to date.

*Pest resistance/susceptibility.*—Believed to be typical of the species.

I claim:

1. A new and distinct *Salvia* plant characterized by the following combination of characteristics:

(a) displays a compact and bushy growth habit, (b) forms in abundance over a long blooming season attractive blossoms that are pale yellow in coloration, (c) displays vigorous large medium green foliage, (d) displays a tendency to vigorously regrow following pruning, and (e) is well suited for providing attractive ornamentation;

substantially as illustrated and described.

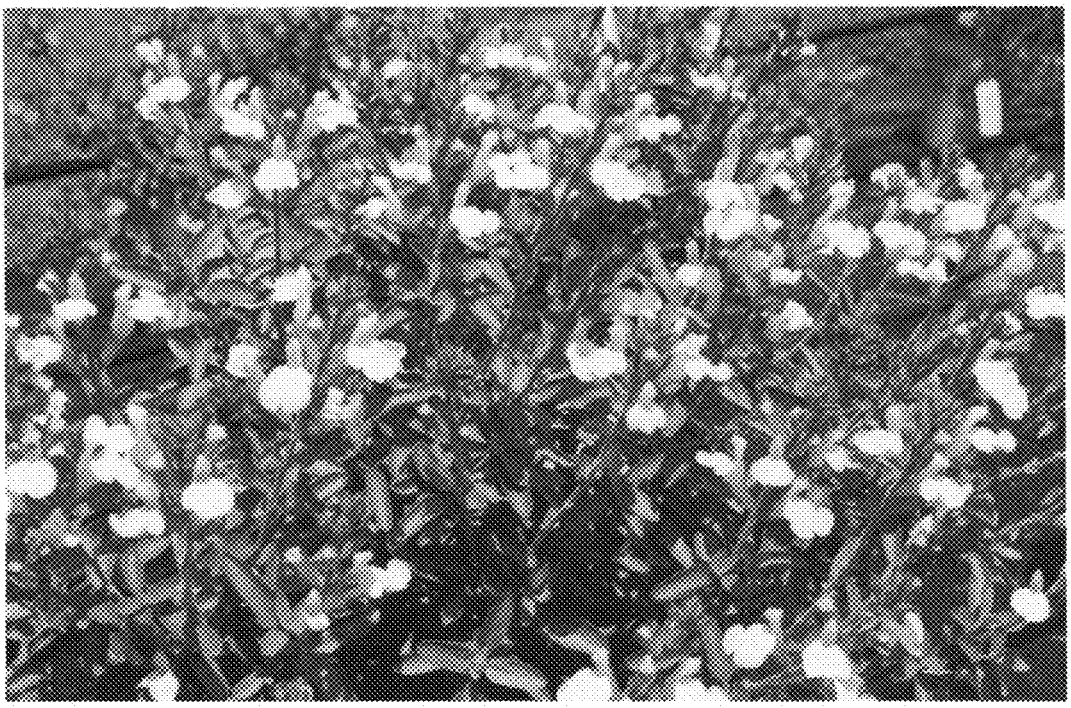

* * * * *